United States Patent [19]

Ross, Jr. et al.

[11] 4,166,021
[45] Aug. 28, 1979

[54] REFERENCE ELECTRODE

[75] Inventors: James W. Ross, Jr., Hull; Martin S. Frant, Newton, both of Mass.

[73] Assignee: Orion Research Inc., Cambridge, Mass.

[21] Appl. No.: 869,363

[22] Filed: Jan. 13, 1978

Related U.S. Application Data

[63] Continuation-in-part of Ser. No. 730,270, Mar. 1, 1977.

[51] Int. Cl.² ............................................. G01N 27/30
[52] U.S. Cl. .................................................. 204/195 F
[58] Field of Search ...................................... 204/195 F

[56] References Cited

U.S. PATENT DOCUMENTS

| | | | |
|---|---|---|---|
| 2,338,713 | 1/1944 | Ewing | 204/195 F |
| 3,438,875 | 4/1969 | Watanabe et al. | 204/195 F |
| 3,498,899 | 3/1970 | Kater et al. | 204/195 F |
| 3,756,936 | 9/1973 | Neuwelt | 204/195 F |

*Primary Examiner*—T. Tung

*Attorney, Agent, or Firm*—John B. Miller; Robert W. Hagopian

[57] ABSTRACT

An improved electrochemical reference electrode for use in potentiometric determinations of species in solution. The body of the electrode is composed of a material substantially permeable to liquid water whose exterior surface, excepting a comparatively small area, is covered by a membrane through which water may pass only by diffusion and which is also ion impermeable. The small area which is not covered forms an opening through the membrane to the body. The body contains a saturated salt slurry. When the electrode is immersed in an aqueous sample solution, water diffuses through the membrane and is transported in bulk across the body. Upon entry into the slurry, the water dissolves the solid salt in the slurry to produce an electrolyte which in turn flows outward through the small area of the body which is not covered by the membrane, whereby a liquid junction is provided between the electrolyte and the sample solution.

12 Claims, 1 Drawing Figure

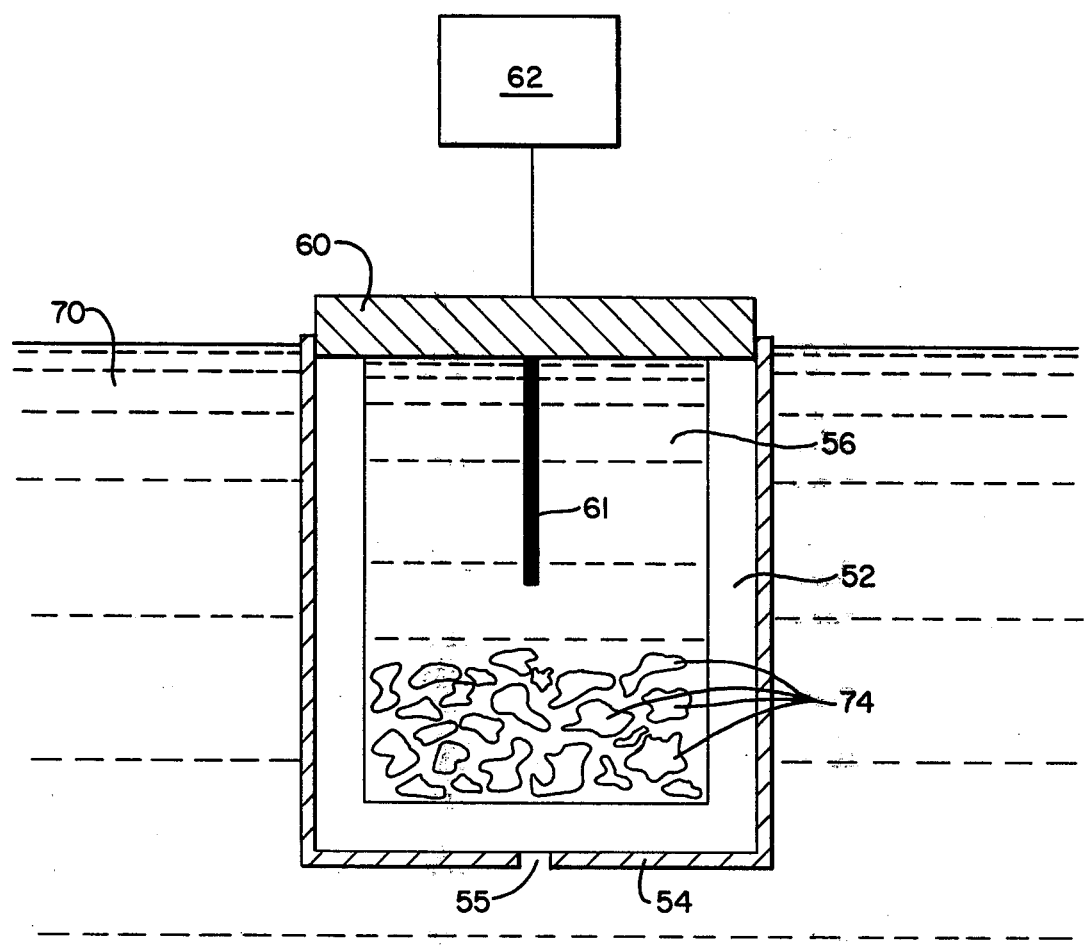

REFERENCE ELECTRODE

This is a continuation-in-part of application Ser. No. 730,270, filed Mar. 1, 1977.

BACKGROUND OF THE INVENTION

1. Field of Invention

This invention relates to electrochemical reference electrodes, and in particular, reference electrodes which are used in potentiometric measurements of the activity of ions in solution.

2. Prior Art Statement

Electrochemical reference electrodes with liquid junctions between the internal electrolyte and the external sample solution are well known in the art as illustrated in U.S. Pat. No. 2,705,220 issued Mar. 29, 1955 to Edward P. Arthur. The general technique of providing a leak structure which permits a controlled flow of electrolyte to sample solution has been the object of liquid junction design for over two decades. Specific liquid junction designs generally recognize that the useful life of reference electrodes is limited by the contamination of the internal electrolyte from inward migration of sample solution through the liquid junction, and by the destruction of the electrical contact between electrolyte and sample solution due to clogging of the liquid junction structure by solids or viscous materials in the sample solution.

Contamination of the internal electrolyte has been controlled by pressurization, as illustrated by U.S. Pat. No. 3,455,793 issued July 15, 1969 to H. Watanabe and E. E. Buzza. Methods similar in principle have been developed in which a constant outflow of electrolyte through the liquid junction shows contamination. These techniques require replenishment of electrolyte throughout the life of the electrodes.

A design which eliminates the clogging problem is illustrated in U.S. Pat. No. 3,486,997 issued Dec. 30, 1969 to Arne J. Petersen. Here, the liquid junction is formed by a valve body positioned within a tube which terminates in an inwardly extending flange providing a central opening in the end of the tube. The valve body includes an enlarged portion positioned inside and freely movable within the tube adjacent to the flange, and a smaller portion protruding through the opening and extending beyond the end of the tube. The body cooperates with the inner surface of the flange to provide a minute passageway through the end of the tube. This design allows the valve body to be moved inwardly by exerting pressure on the protruding portion, so that clogging materials can be flushed out of the liquid junction. However, the Petersen device does not eliminate the contamination problem since inward migration from the test solution is not restricted when the reference electrode is in normal use.

The present invention is designed to eliminate the contamination and clogging problem. An additional benefit includes self-replenishment of electrolyte, thus eliminating the danger of dry-up and increasing the efficiency and lifetime of the reference electrode use.

SUMMARY OF INVENTION

The primary object of applicant's invention is to provide a non-contaminating, non-clogging reference electrode for use in potentiometric measurements. Another object is to provide a reference electrode with long-term service capability.

These and other objects of the present invention are effected by providing a reference electrode having a body composed of a material substantially permeable to liquid water whose exterior surface, excepting a comparatively small area, is covered by a membrane through which water may pass only by diffusion and which is also ion impermeable. The small area which is not covered forms an opening through the membrane to the body. The body contains a saturated salt slurry. When the electrode is immersed in an aqueous sample solution, water diffuses through the membrane, and is transported in bulk across the body. Upon entry into the slurry, the water dissolves the solid salt in the slurry to produce an electrolyte which in turn flows outward through the small area of the body which is not covered by the membrane whereby a liquid junction is provided between the electrolyte and the sample solution.

These and other objects, aspects, and advantages of the present invention will become more apparent with the following specification and the scope of the application of which will be indicated in the claims.

BRIEF DESCRIPTION OF THE DRAWINGS

For a more full understanding of the nature and objects of the invention, reference should be made to the following detailed description taken in connection with the accompanying drawing which shows a diagrammatic side-elevational, cross-sectional view of a preferred form of a reference electrode embodying the present invention.

PREFERRED EMBODIMENT

Referring now to the drawing, there is shown a reference electrode embodying the principles of the present invention. The body 52 is an elongated hollow tube open at one end. The usual shape of the body is typically circular, although other forms are within the scope of the invention and are intended to be included in this disclosure. The body is composed of a material, typically porous ceramic, that is substantially rigid and liquid water permeable, and substantially chemically inert to the solutions with which the reference electrode might be placed in contact. By liquid water permeable, it is meant that water transports through the body when a pressure gradient exists across the wall of the body.

Exteriorly mounted upon and directly contacting the exterior surface area of the body 52 is membrane 54 which is composed of a material which is ion impermeable and through which water may only pass by diffusion, that is, by vaporizing or dissolving, and not by bulk liquid transport. In other words, water will pass through the membrane due to a concentration gradient across the membrane, but not due to a pressure gradient across the membrane. Examples of such membrane materials are: silicone rubber, microporous polyethylene, polyvinylchloride, teflon, or similar material.

Silicone rubber is available as Ja Bar Formulation 5509 from Ja-Bar, Inc., Andover, Md. Microprorous polyethylene is available as POREX ® from the Porex Materials Corporation, Atlanta, Ga.

Microporous polyvinylchloride is available from Millipore Corporation of Bedford, Mass. as Fluoropore ® (formerly Polyvic ®). Microporous teflon is available as Gore-Tex from W. L. Gore & Associates, Inc., Elkton, Md.

Additionally, this material must be substantially chemically inert to solutions with which the reference electrode might be placed in contact. All of the exterior surface of the body is covered by the membrane with the exception of a comparatively small area which forms an opening 55 in the membrane 54 to the body 52. Geometrical variations in the size, shape and location of the opening 55 are nondistinct from the principles of the invention, and intended to be included in this disclosure.

A solid salt slurry 74 is placed inside the body 52 and in electrical contact with reference element 61, typically the well known Ag.AgCl or Hg.Hg$_2$Cl$_2$ calomel element. The composition of the salt is typically potassium chloride, KCl, or potassium nitrate, KNO$_3$, but any other equitransferent salt is also suitable, and is intended to be included in this disclosure. The salt is typically provided in solution form as a saturated salt slurry. The body 52 is sealed with an impervious cap 60. The reference element is electrically connected to an electrometric device 62 which measures the potential developed when the electrode is placed in the sample solution.

When the electrode is immersed in test solution 70, water diffuses through the membrane 54 by vaporization or dissolving, and is transported across body 52 in bulk. The direction of the water movement is inward through the membrane 54 and body 52 due to the relatively high concentration of the salt inside the body. This difference in salt concentration causes an osmotic pressure build up within the body. The diffusion rate is a function of membrane thickness, membrane surface area, and the permeability of the membrane material. The inflowing water dissolves the solid salt 74 to form reference electrolyte 56. The electrolyte 56 flows through the opening 55 in the membrane 54 to form a liquid junction between the electrolyte 56 and the sample solution 70. This flow is due to a hydrostatic pressure difference resulting from the osmotic pressure difference between the sample solution 70 and the reference electrolyte 56. The osmotic pressure difference is due to the relatively higher concentration of the salt inside the body. The electrolyte flows out because of the pressure buildup in the body 52. If the comparative areas of the membrane and the opening 55 are such that more water can be transported through the membrane 54 than saturated salt solution can be emitted through the opening 55, the internal pressure will build up until a steady state condition is reached wherein the rate of water transport in through the membrane 54 matches the rate of saturated salt solution flow out through the opening 55. The rate of outflow determines the rate at which solid salt 74 is dissolved in the electrolyte, allowing the useful life of the electrode to be controlled by the amount of solid salt placed in the saturated electrolyte.

Since various changes may be made in the above apparatus without departing from the scope of the present invention, it is intended that all matter contained in the above description or shown in the accompanying drawing shall be interpreted in an illustrative and not in a limiting sense.

What is claimed is:

1. An electrochemical reference electrode for use in potentiometric determinations of species in an aqueous sample solution, comprising:
   a body, composed of a material substantially permeable to liquid water;
   a membrane directly contacting and surrounding the entire exterior surface of the body excepting an area which forms an opening in the membrane to the surface of the body, said membrane being composed of a material through which water may pass by diffusion, but not by bulk transport, and which is also ion impermeable;
   a reference electrolyte placed inside the body of the electrode, composed of a saturated salt slurry, and forming a liquid junction with the sample solution at the surface of the body not covered by the membrane; and
   a reference element immersed in the reference electrolyte.

2. An electrochemical reference electrode as recited in claim 1 wherein the area of the surface of the body not contacted by the membrane is comparatively small in relation to the total surface area.

3. An electrochemical reference electrode as recited in claim 1 further comprising electrometric means for measuring the electric potential developed by the reference electrode when placed in contact with the solution.

4. An electrochemical reference electrode as recited in claim 1 wherein said body is composed of porous ceramic.

5. An electrochemical reference electrode as recited in claim 1 wherein said membrane is composed of silicone rubber.

6. An electrochemical reference electrode as recited in claim 1 wherein said membrane is composed of microporous polyethylene.

7. An electrochemical reference electrode as recited in claim 1 wherein said membrane is composed of microporous polyvinylchloride.

8. An electrochemical reference electrode as recited in claim 1 wherein said membrane is composed of microporous liquid water impermeable teflon.

9. An electrochemical reference electrode as recited in claim 1 wherein said reference electrolyte is an aqueous saturated KCl slurry.

10. An electrochemical reference electrode as recited in claim 1 wherein said reference electrolyte is an aqueous saturated KNO$_3$ slurry.

11. An electrochemical reference electrode as recited in claim 1 wherein said reference element is composed of Ag.AgCl.

12. An electrochemical reference electrode as recited in claim 1 wherein said reference element is composed of Hg.Hg$_2$Cl$_2$.

* * * * *